United States Patent [19]

Marshall et al.

[11] Patent Number: 4,777,299

[45] Date of Patent: Oct. 11, 1988

[54] PROCESS FOR LEUKOTRIENE ANTAGONISTS

[75] Inventors: Winston S. Marshall, Bargersville; Sandra K. Sigmund, Indianapolis; Celia A. Whitesitt, Greenwood, all of Ind.

[73] Assignee: Eli Lilly and Company, Indianapolis, Ind.

[21] Appl. No.: 142,112

[22] Filed: Jan. 11, 1988

Related U.S. Application Data

[63] Continuation of Ser. No. 64,900, Jun. 19, 1987, abandoned.

[51] Int. Cl.$^4$ .............................................. C07C 45/00
[52] U.S. Cl. .................................................... 568/319
[58] Field of Search .......................................... 508/319

[56] References Cited

U.S. PATENT DOCUMENTS 4,661,505 4/1987 Marshall et al. .................... 568/437

FOREIGN PATENT DOCUMENTS 59-65039 4/1984 Japan ..................................... 568/319

OTHER PUBLICATIONS

P. Da Re and L. Cimatoribus, *Journal of Organic Chemistry*, 26, pp. 3650-3653 (1961).

G. P. Schiemenz and U. Schmidt, *Liebigs Annalen der Chemie*, pp. 1514-1519 (1976).

J. March, *Advanced Organic Chemistry-Reactions, Mechanism, and Structure*, Second Edition, McGraw-Hill Book Company, New York, pp. 394-395 (1977).

*Primary Examiner*—James H. Reamer
*Attorney, Agent, or Firm*—Robert A. Conrad; Leroy Whitaker

[57] ABSTRACT

1,3-Dialkylbenzenes are acylated and deprotected in a mixture of acetic or propionic acid and hydrobromic acid. The dihydroxyphenones thus produced are intermediates in the synthesis of leukotriene antagonists.

11 Claims, No Drawings

PROCESS FOR LEUKOTRIENE ANTAGONISTS

This application is a continuation, of application Ser. No. 07/064,900, filed June 19, 1987 now abandoned.

3'-(Substituted or unsubstituted) dihydroxyphenones of the Formula A

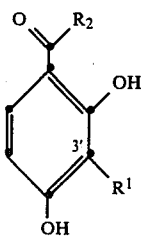

are important intermediates in the synthesis of leukotriene antagonist compounds, especially compounds of Formula B

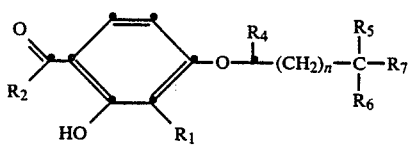

The compounds of Formula B are the subject of Marshall et al., U.S. Pat. No. 4,661,505, issued April 28, 1987. The compounds of Formula B treat allergic disorders such as asthma, where leukotrienes are thought to be the causal mediators.

In the past, the phenones of Formula A have been prepared in a multi-step process. Commercially available 1,3-dialkoxybenzenes (e.g., 1,3-dimethoxybenzene) was reacted with a strong base (such as n-butyl lithium) and the resultant phenyl anion was alkylated with the appropriate $R_1$ substituent (for example, n-propyl iodide). The 2-substituted dimethoxybenzene was next acylated under Friedel-Crafts conditions (such as acetyl chloride in the presence of aluminum trichloride), and finally the acylated analog was subjected to conditions that removed the alkyl moieties of the original two alkoxy substituents of the benzene ring. Alternately, the order of the acylation and deprotection steps were sometimes reversed.

Quite unexpectedly, we have found conditions to do both the acylation and deprotection reactions at the same time. The conditions are such that there is no need to use (and thus properly dispose of it) the Lewis acid traditionally associated with the Friedel-Crafts acylation step. The instant invention simplifies the synthesis and thus lowers the cost of leukotriene antagonists such as those of the above Formula B.

SUMMARY OF THE INVENTION

The invention is directed to a process for making a phenone of the Formula I

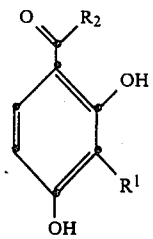

which comprises combining a dialkoxybenzene of the Formula II

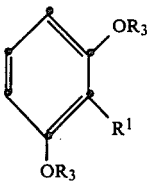

with a carboxylic acid of the Formula III $$R_2COOH \qquad III$$

and hydrobromic acid from between about the boiling point of the reaction mixture to about 75° C. for between about one hour to about five days, and wherein $R_1$, $R_2$, and $R_3$ are as defined below.

DETAILED DESCRIPTION OF THE INVENTION

The instant invention is directed to a process for making a compound of the formula:

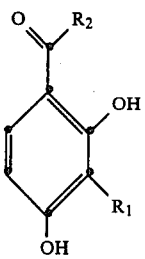

which comprises combining a compound of the formula:

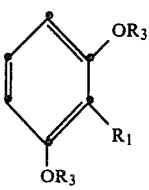

with a carboxylic acid of the formula:

and hydrobromic acid from between about the boiling temperature of the reaction mixture to about 75° C. for between about one hour until about five days; and wherein:

$R_1$ is hydrogen, $C_1$ to $C_{10}$ alkyl, or $C_2$ to $C_6$ alkenyl;
$R_2$ is methyl or ethyl; and
$R_3$ is methyl or ethyl.

In the above process, the term "$C_1$ to $C_{10}$ alkyl" refers to the straight and branched aliphatic radicals of 1 to 10 carbon atoms such as methyl, ethyl, propyl, isopropyl, butyl, isobutyl, sec-butyl, tertbutyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like.

The term "$C_2$ to $C_6$ alkenyl" refers to straight and branched radicals of two to six carbon atoms such as ethenyl, allyl, isopropenyl, butenyl, isobutenyl, 3-methyl-2-butenyl, n-hexenyl, and the like.

The stoichiometry of the above reaction is not critical. It is preferred that at least about one equivalent of the carboxylic acid of Formula III per equivalent of the dialkoxybenzene of Formula II be present, with an excess of the acid preferred. The hydrobromic acid can be present in only a catalytic amount, although an equimolar or an excess amount in relation to the dialkoxybenzene is preferred. When the carboxylic acid of Formula III is acetic acid, several commercial preparations are available, the most convenient for use in the process being glacial acetic acid. Propionic acid can be obtained commercially as a 99% solution. The 99% solution can be used as is or diluted with water before using in the process.

Similarly, the hydrobromic acid reagent for the process is conveniently supplied by the commercial preparation of 48% hydrobromic acid in water. However, aqueous solutions containing as little as 10% to saturated aqueous solutions of hydrobromic acid can be made in the conventional manner and used in the process. Alternatively, hydrogen bromide gas can be bubbled through the acetic or propionic acid to give the appropriate mixture of the two acids.

The order of addition of the dialkoxybenzene and carboxylic acid starting materials and the hydrobromic acid are not critical. Typically, the dialkoxybenzene is dissolved in the carboxylic acid then the hydrobromic acid is added, or the acid mixture is added to the dialkoxybenzene substrate.

The progress of the process is dependent on the concentration of the two acids and the temperature of the reaction mixture. The higher the concentration of acids, the faster the reaction proceeds. The progress can be monitored in the usual chromatographic and spectroscopic ways—such as by analyzing aliquots of the reaction mixture by nuclear magnetic resonance spectroscopy, thin layer chromatography, column chromatography, gas chromatography, or high pressure liquid chromatography. For instance, a small aliquot (e.g. 0.10 ml) can be withdrawn at an appropriate time, partitioned between water and ether, and the ether layer evaporated (the ether layer may additionally be washed with brine and dried over sodium or magnesium sulfate). The resultant residue can then be analyzed for presence of starting material and desired product by the analytical method of choice.

The time period for the process is most dependent on the concentration of the carboxylic and hydrobromic acids. The time period for the reaction to be substantially complete is from between about one hour to about 5 days, with approximately 12 to 48 hours typical. Higher yields and shorter reaction times are obtained when excess amounts of both the carboxylic and hydrobromic acids in relation to the dialkoxybenzene is used. Also, the best conditions for the reaction include those wherein the mixture of acids is anhydrous. For example, hydrogen bromide gas can be bubbled through glacial acetic acid prior to the reaction to obtain the appropriate mixture of acids. The temperature is also a critical factor in the time required for the process. The temperature should be the boiling point of the reaction mixture (typically 100°–110° C.) to about 75° C., with the boiling point of the mixture preferred.

The phenone product of the instant process is isolated by conventional methods. For instance, the reaction mixture can be extracted with an ether/water mixture. The ether layer can be further treated with brine and a suitable solid drying agent (such as sodium or magnesium sulfate) then concentrated to a residue. Alternately, the ether level could immediately be concentrated to a foam. The product can be used as is from this isolation, or can be purified by chromatographic techniques. One such technique is high pressure liquid chromatography on a silica gel column eluted with a gradient of 5 to 15% of ethyl acetate in hexane.

There are several preferred embodiments of the instant process. The broadest of these occurs when $R_3$ is methyl. More preferred embodiments occur (in increasing order of importance) when $R_2$ is either methyl or ethyl, $R_1$ is $C_1$ to $C_{10}$ alkyl, $C_3$ to $C_8$ alkyl, and n-propyl. The other most preferred embodiment (when $R_2$ is methyl) occurs when $R_1$ is hydrogen.

As discussed above, the products of the present process are starting materials for the synthesis of leukotriene antagonists. The products are especially useful for the synthesis of leukotriene antagonists of the above Formula B, which compounds are discussed in W. S. Marshall et al., U.S. Pat. No. 4,661,505, issued Apr. 28, 1987, herein incorporated by reference. A particularly useful pharmaceutical compound encompassed by the Marshall et al. patent is LY171883, which has the formula:

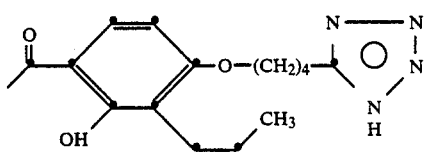

LY171883 is currently undergoing clinical trials in the United States and in various European countries as an antiasthmatic compound. The phenone products of the present process are alkylated on the 4'-hydroxy group with a compound of the formula

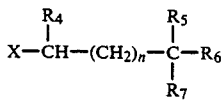

as discussed in columns 3 and 4 of the Marshall et al. patent. A product of the present process (Formula A, wherein $R_2$ is methyl and $R_1$ is n-propyl) is an intermediate in the synthesis of LY171883.

The 1,3-dialkoxy-2-(substituted and unsubstituted)-benzene starting materials for the instant process are made by well-known procedures. Specifically, the 1,3-dialkoxybenzene is converted to a phenyl anion by strong base and alkylated by the appropriate derivative of $R^1$. (A specific example of such an alkylation procedure is given below as Preparation 1 and a part of Example 2). All other reagents and starting materials for the process are either commercially available or at least their preparation is well known in the art.

The following Preparations and Examples are provided to further illustrate the instant invention. The Preparations and Examples are for the benefit of those skilled in the art and are not to limit the scope of the invention in any way. Abbreviations used in the Preparations and Examples are standard ones well known in the art; thus "THF", "DMSO", "HPLC", "n.m.r" stand for tetrahydrofuran, dimethylsulfoxide, high pressure liquid chromatography, and nuclear magnetic resonance, respectively. Unless otherwise noted, HPLC results were obtained on a Waters Prep ® LC 500A instrument using Prepak ®-500/Silica cartridges. The n.m.r. data reported below were obtained on a General Electric QE-300 300 MHz instrument in $CDCl_3$. The chemical shifts are referenced to TMS. In describing the n.m.r. spectra, "s" stands for singlet, "d" means a doublet, "t" means a triplet and "m" signifies a multiplet.

Preparation 1

1,3-Dimethoxy-2-(hept-1-yl)benzene 1,3-dimethoxybenzene (0.25 mol, 34 ml) was dissolved in THF (1 liter, dried) and the resultant solution was cooled in an ice bath. n-Butyl lithium (200 ml, 0.32 moles) was added over a period of one hour. The resultant solution was stirred for 2 hours in an ice bath. Solution was then cooled to −78° C. and n-heptyl iodide (226 ml, 0.22 moles) was quickly added. The solution was then allowed to warm to room temperature and stirred overnight then refluxed for 2 hours. The solution was cooled and a mixture of diethyl ether and water was added. The ether layer was collected, dried over magnesium sulfate, filtered and evaporated to dryness. The residue was chromatographed by HPLC (eluted with hexane) to yield 34.0 g of the title product.

EXAMPLE 1

3'-(n-Propyl)-2',4'-dihydroxyacetophenone

Procedure A 1,3-Dimethoxy-2-(prop-1'-yl)benzene (0.36 g, 2.0 mmol) was dissolved in acetic acid (15 ml). 48% hydrobromic acid (9 ml) was added to the stirring solution and the solution was heated to reflux and the reaction progress monitored by gas chromatography. After the solution had refluxed for a period of 8 days and 20 hours, chromatographic analysis demonstrated that 71% of the title product was present. The reaction mixture was worked up by partitioning it between water and ether. The ether phase was dried over magnesium sulfate then evaporated to dryness to yield predominantly the title product plus a small amount of 1,3-dihydroxy-2-propylbenzene.

Procedure B 1,3-Dimethoxy-2-(prop-1'-yl)benzene (3.6 g, 2.0 mmol) was dissolved in acetic acid (30 ml). To the stirring solution was added 48% hydrobromic acid (18 ml) and the resultant solution was heated to reflux temperature. The progress of the reaction was monitored by gas chromatography. After 66.5 hours at these conditions, chromatographic analysis demonstrated that the mixture contained 68% of the title product. The title product was isolated by partitioning the reaction mixture between water and ether. The ether phase was then dried over magnesium sulfate, then evaporated to dryness. (The progress of the reaction was monitored by taking small aliquots of the reaction solution worked up as described immediately before, and dissolving the residue in acetone before chromatographic analysis.

Procedure C 1,3-Dimethoxy-2-(prop-1'-yl)benzene (0.36 g, 2.0 mmol) was dissolved in acetic acid (75 ml). 48% Hydrobromic acid (45 ml) was added and the reaction solution was stirred and heated to reflux. The progress of this reaction was followed by gas chromatography. Chromatographic analysis demonstrated that after 19 hours at reflux, approximately 73% of the title product was present. The reaction mixture was worked up as described for the above two preparations.

EXAMPLE 2

3'-(iso-Propyl)-2',4'-dihydroxyacetophenone

Under a nitrogen atmosphere, 1,3-dimethoxybenzene (33 ml) was dissolved in THF (1l). The solution was cooled in an ice bath then n-butyl lithium (200 ml) was added in a dropwise fashion in over a 45 minute period. The resultant mixture was stirred for 2 hours at a temperature of 10° C. The solution was then cooled to 0° C. and acetone (21 ml) was added in a dropwise fashion. Solution was stirred at room temperature overnight. The reaction mixture was partitioned between ethyl acetate and water. The ethyl acetate layer was dried over sodium sulfate and the solvent removed. The residue was dissolved in a mixture of ethyl acetate (50 ml) and sulfuric acid (1 ml). The acidic mixture was subjected to a positive hydrogen pressure (30 psi) over a catalytic amount of 5% palladium-on-carbon in a Parr shaker at room temperature for 30 minutes. The solution was filtered and water added. The organic layer was purified by HPLC (eluted with a gradient of 0 to 5% hexane in ethyl acetate) to yield 6.3 g of 1,3-dimethoxy-2-(iso-propyl)benzene. This latter substituted benzene product was refluxed for 3 days in a mixture of 48% hydrobromic acid in water and acetic acid (300 ml to 500 ml). Ether and brine were added to the reaction mixture. The ether layer was washed with brine, dried over magnesium sulfate, filtered, and evaporated to dryness. The residue was chromatographed by HPLC (column eluted with a gradient of 5 to 15% ethyl acetate in hexane). The chromatography yielded 1.82 g of the title product.

n.m.r.: δ13.1 (1H, s), 7.5 (1H, d), 6.3 (1H, d), 3.5 (1H, m), 2.6 (3H, s), 1.4 (6H, d).

EXAMPLE 3

2',4'-dihydroxyacetophenone 1,3-Dimethoxybenzene (8.00 g, 57.4 % mmol) was combined with acetic acid (500 ml) and 48% hydrobromic acid (300 ml). The solution was stirred and heated to reflux for five days. The reaction mixture was allowed to cool to room temperature then poured into water (500 ml). The aqueous solution was extracted with ether (500 ml, 2×) and concentrated in vacuo to a reddish brown oil. Chromatography by HPLC yielded a small amount of the title product uncontaminated by the resorcinol side product:

n.m.r.: $\delta$12.70 (s, 1H), 7.63 (d, 1H), 6.40 (d, 1H), 6.38 (s, 1H), 2.56 (s, 3H).

EXAMPLE 4

3'-(iso-Butyl)-2',4'-dihydroxyacetophenone 1,3-Dimethoxy-2-(iso-butyl)benzene (11.3 g) was dissolved in acetic acid (250 ml) and 48% hydrobromic acid (150 ml). The resultant solution was heated to reflux for 2 days, cooled, and ether and water added. The ether layer was washed with brine (2×), dried over sodium sulfate, filtered and evaporated to dryness. The concentrate was chromatographed by HPLC (column eluted with a gradient of 1 to 10% ethyl acetate in hexane) to yield 3.87 g of the title product.

n.m.r.: $\delta$12.8 (1H, s), 7.6 (1H, d), 6.4 (1H, d), 5.4 (1H, s), 2.6 (3H, s), 2.55 (2H, d), 2.0 (1H, m), 1.0 (6H, d).

EXAMPLE 5

3'-(Pent-1"-yl)-2',4'-Dihydroxyacetophenone 1,3-Dimethoxy-2-(pentyl-1'-yl)benzene (14.0 g) was added to 48% hydrobromic acid (300 ml) and acetic acid (500 ml) then the resultant mixture was heated to reflux for 2 days. The mixture was cooled and diethyl ether in water were added. The ether layer was washed with brine (2×), dried over sodium sulfate, filtered, and evaporated to dryness. The residue was chromatographed by HPLC (column eluted with a 5 to 15% ethyl acetate in hexane gradient) to yield 5.9 g of the title product.

n.m.r.: $\delta$13.0 (1H, s), 7.6 (1H, d), 6.4 (1H, d), 4.8 (1H, s), 2.65 (2H, m), 2.6 (3H, s), 1.6 (4H, broad s), 1.4 (2H, broad s), 1.0 (3H,t).

EXAMPLE 6

3'-(Hex-1"-yl)-2',4'-Dihydroxyacetophenone 1,3-Dimethoxy-2-(hex-1"-yl)benzene (14.8 g) was combined with 48% hydrobromic acid (300 ml) and acetic acid (500 ml). The mixture was heated to reflux for 2 days. The reaction mixture was cooled and a mixture of diethyl ether and brine were added, and the diethyl ether layer was separated. The ether layer was washed with brine (2×), dried over sodium sulfate, filtered, and evaporated to dryness. The crude product was purified as in Example 5 to give 6.1 g of the title product.

n.m.r.: $\delta$13.1 (1H, s), 7.6 (1H, d), 6.4 (1H, d), 4.9 (1H, s), 2.65 (2H, t), 2.6 (3H, s), 1.6 (2H, m), 1.3 (6H, m), 0.9 (3H, t).

EXAMPLE 7

3'-(Hept-1"-yl)-2',4'-Dihydroxyacetophenone 1,3-Dimethoxy-2-(hept-1"-yl)benzene (34 g) was reacted with 48% hydrobromic acid and acetic acid and the reaction mixture was treated as in the preceding Example 6. The concentrate was chromatographed by HPLC (column eluted with a 1 to 15% ethyl acetate in hexane solution) to yield 5.84 g of the title product.

n.m.r.: 13.1 (1H, s), 7.5 (1H, d), 6.4 (1H, d), 4.9 (1H, s), 2.65 (2H, t), 2.6 (3H, s), 1.6 (2H, m), 1.3 (8H, m), 0.9 (3H, t).

EXAMPLE 8

3'-(Oct-1"-yl)-2',4'-Dihydroxyacetophenone 1,3-Dimethoxy-2-(oct-1"-yl)benzene (31.29 g) was added to 48% hydrobromic acid (300 ml) and acetic acid (500 ml) and the mixture was heated to reflux for 3 days. The reaction mixture was cooled and brine and ether were added. The ether layer was filtered (to remove polymer solid), separated, washed with water (3×), dried over sodium sulfate, filtered, and evaporated to dryness. The resultant concentrate was chromatographed by HPLC (column eluted with 5 to 15% ethyl acetate in hexane) to yield 2.5 g of the title product. Slightly impure fractions containing the title product combined and recrystallized from mixture of ethyl acetate in hexane to yield 11 g of the title product.

n.m.r.: $\delta$13.1 (s, 1H), 7.5 (d, 1H), 6.4 (d, 1H), 5.4% (s, 1H), 2.65 (t, 2H), 2.6 (s, 3H), 1.6 (m, 2H), 1.3 (m, 10H), 0.9 (t, 3H).

Analysis Calculated for $C_{16}H_{24}O_3$: Theory: C, 72.69; H, 9.15; Found: C, 72.78; H, 9.28.

EXAMPLE 9

1-(Propionyl)-2,4-Dihydroxy-3-(n-Propyl)benzene 1,3-Dimethoxy-2-(prop-1'-yl) benzene (0.90 g, 5.0 mmole) was dissolved in propionic acid (150 ml) and 48% aqueous hydrobromic acid (90 ml, 795 mmol HBr) was added. The resultant reaction solution was refluxed for 3 days. The reaction solution was cooled, added to water (250 ml) then extracted with ether (300 ml, 2×). The organic phases were combined, washed with brine (100 ml), dried over magnesium sulfate and concentrated in vacuo to a reddish brown oil. The oil was subjected to flash chromatopraphy over Kieselgel 60 (230-400 mesh, 4 cm diameter×16 cm length) eluted with a step gradient of 1% to 5% ethyl acetate in hexane. The chromatography yielded 0.33 g, 32% of the title product:

n.m.r.: $\delta$13.08 (s, 1H), 7.54 (d, 1H), 6.37 (d, 1H), 5.92 (s, 1H), 2.95 (q, 2H), 2.63 (t, 2H), 1.58 (m, 2H), 1.23 (t, 3H), 0.97 (t, 3H).

EXAMPLE 10

3'-(n-Propyl)-2',4'-Dihydroxyacetophenone 1,3-Dimethoxy-2-(n-propyl)benzene (0.90 g, 5.0 mmol), 48% aqueous hydrobromic acid (30 ml, 265 mmol), and glacial acetic acid (150 ml) were combined and stirred at reflux temperature for 72 hours. The reaction mixture was cooled to room temperature then added to water (250 ml). The aqueous mixture was extracted with ether (500 ml, 2×). The organic phases were combined, washed with brine (100 ml), dried over magnesium sulfate and concentrated in vacuo. The residue was flash chromatographed over Kieselgel 60 (230-400 mesh, 4 cm diameter×16 cm length) eluted with 1% ethyl acetate in hexane, followed by a step gradient (2%, 3%, 4%) of ethyl acetate in hexane to give 0.4 g, 41% of the title product.

n.m.r.: δ12.97 (s, 1H), 7.52 (d, 1H), 6.38 (d, 1H), 5.79 (s, 1H), 2.63 (t, 2H), 2.56 (s, 3H), 1.58 (m, 2H), 0.98(t, 3H).

EXAMPLE 11

2',4'-Dihydroxyacetophenone from 1,3-Diethoxybenzene 1,3-Diethoxybenzene (0.84 g, 5.1 mmol) glacial acetic acid (150 ml), and 48% aqueous hydrobromic acid (30 ml, 265 mmol of HBr) were combined and stirred at reflux temperature for four days. The reaction solution was permitted to cool to room temperature, was poured into water (500 ml) and the aqueous solution was extracted with ether (2×, 500 ml). The ether layers were combined, washed with brine, dried over magnesium sulfate and taken to dryness in vacuo. Chromatography as in Examples 12 and 13 will yield the title product.

EXAMPLE 12

3'-(n-Propyl)-2',4'-Dihydroxyacetophenone from a 10:1 Acid Mixture 1,3-Dimethoxy-2-propylbenzene (0.90 g, 5.0 mmol), glacial acetic acid (150 ml), and 48% aqueous hydrobromic acid (15 ml, 133 mmol) were combined and stirred at reflux temperature for three days. The mixture was allowed to cool to room temperature; poured into water (500 ml), and the aqueous solution extracted with ether (500 ml, 2×). The ether layers were combined, washed with brine, dried over magnesium sulfate, filtered and taken to dryness in vacuo. Flash chromatography as in Example 10 (plus an additional step of 5% ethyl acetate in hexane) yielded the title product: n.m.r.: δ12.97 (s, 1H), 7.52 (d, 1H), 6.38 (d, 1H), 5.79 (s, 1H), 2.63 (t, 2H), 2.56 (s, 3H), 1.58 (m, 2H), 0.98 (t, 3H).

EXAMPLE 13

3'-(n-Propyl)-2',4'-Dihydroxyacetophenone from an Anhydrous Mixture of the Acids.

Glacial acetic acid (350 ml) absorbed 19.4 g of hydrogen bromide gas to give a 5% hydrogen bromide in acetic acid solution.

1,3-Dimethoxy-2-(n-propyl)benzene (0.90 g, 5.0 mmol) was dissolved in 5% hydrogen bromide/glacial acetic acid solution and the reaction solution was stirred at reflux temperature for 17 hours then at room temperature for 12 hours. The reaction solution was added to water (500 ml) and the aqueous solution was extracted with ether (2×500 ml). The organic layers were combined, treated and chromatographed as in Example 10 (except that this Example used an additional elution of 5% ethyl acetate in hexane) to yield 0.61 g, 63% of the title product.

n.m.r.: δ12.99, (s, 1H), 7.5, (d, 1H), 6.38 (d, 1H), 2.63 (t, 2H), 2.56 (s, 3H), 1.57 (m, 2H), 0.98 (t, 3H).

We claim:

1. A process for making a compound of the formula

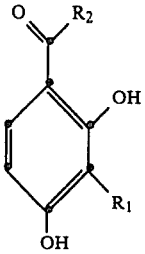

which comprises combining a compound of the formula:

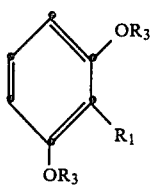

with a carboxylic acid of the formula

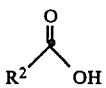

and hydrobromic acid from between about the boiling temperature of the reaction mixture to about 75° C. for between about one hour until about five days; and wherein:

$R_1$ is hydrogen, $C_1$ to $C_{10}$ alkyl, or $C_2$ to $C_6$ alkenyl;
$R_2$ is methyl or ethyl; and
$R_3$ is methyl or ethyl.

2. A process of claim 1, wherein $R_3$ is methyl.
3. A process of claim 2, wherein $R_2$ is methyl.
4. A process of claim 3, wherein $R_1$ is $C_1$ to $C_{10}$ alkyl.
5. A process of claim 4, wherein $R_1$ is $C_3$ to $C_8$ alkyl
6. A process of claim 5, wherein $R_1$ is n-propyl.
7. A process of claim 3, wherein $R_1$ is hydrogen.
8. A process of claim 2, wherein $R_2$ is ethyl.
9. A process of claim 8, wherein $R_1$ is $C_1$ to $C_{10}$ alkyl.
10. A process of claim 9, wherein $R_1$ is $C_3$ to $C_8$ alkyl.
11. A process of claim 10, wherein $R_1$ is methyl.

* * * * *